United States Patent [19]
Kozuma et al.

[11] Patent Number: 6,046,018
[45] Date of Patent: Apr. 4, 2000

[54] HIGHLY SENSITIVE METHOD FOR ASSAYING CHIRO-INOSITOL AND COMPOSITIONS FOR THE ASSAY

[75] Inventors: Takuji Kozuma; Mamoru Takahashi, both of Shizuoka, Japan

[73] Assignee: Asahi Kasei Kogyo Kabushiki Kaisha, Osaka, Japan

[21] Appl. No.: 09/308,575

[22] PCT Filed: Mar. 20, 1998

[86] PCT No.: PCT/JP98/01215

§ 371 Date: Jun. 8, 1999

§ 102(e) Date: Jun. 8, 1999

[87] PCT Pub. No.: WO98/42863

PCT Pub. Date: Jan. 10, 1998

[30] Foreign Application Priority Data

Mar. 26, 1997 [JP] Japan .................................. 9-072878

[51] Int. Cl.[7] .............................. C12Q 1/32; C12Q 1/26; C12Q 1/54
[52] U.S. Cl. ............................... 435/26; 435/25; 435/14; 435/4; 526/4.1; 526/1.1; 526/26.24
[58] Field of Search .................. 435/26, 25, 14, 435/4; 536/4.1, 1.1, 26.24

[56] References Cited

U.S. PATENT DOCUMENTS

| 5,091,596 | 2/1992 | Kennington et al. | 435/26 |
| 5,183,764 | 2/1993 | Kennington et al. | 435/26 |
| 5,356,790 | 10/1994 | Ueda et al. | 435/26 |

FOREIGN PATENT DOCUMENTS

| 8-21835 | 1/1996 | Japan . |
| WO 90/10711 | 9/1990 | WIPO . |
| WO 91/12335 | 8/1991 | WIPO . |
| 9842863 | 10/1998 | WIPO . |

OTHER PUBLICATIONS

A. Kennington et al., "Low Urinary chiro–Inositol Excretion in Non–Insulin–Dependent Diabetes Mellitus", *The New England Journal of Medicine,* vol. 323, No. 6, 1990, pp. 373–378.

T. Niwa et al., "Gas Chromatographic–Mass Spectrometric Analysis of Polyols in Urine and Serum of Uremic Patients", *Journal of Chromatography,* vol. 277, 1983, pp. 25–39.

(List continued on next page.)

*Primary Examiner*—Louise N. Leary
*Attorney, Agent, or Firm*—Young & Thompson

[57] ABSTRACT

The present invention relates to an assay method of chiroinositol which comprises reacting a specimen containing chiroinositol with

1) a dehydrogenase, which catalyses at least reversible reaction with a substrate of chiroinositol in the presence of a coenzyme selected from NAD(P)s and a coenzyme selected from thio-NAD(P)s,
2) A1 and
3) B1 to form cycling reaction of the formula

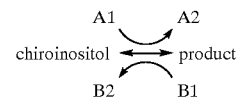

wherein a product is a compound, from which 2 or 4 hydrogen atoms are deleted from chiroinositol, A1 is NAD(P)s or thio-NAD(P)s, A2 is a reduced form of A1, B1 is a reduced form of NAD(P)s in case of A1 being thio-NAD(P)s or a reduced form of thio-NAD(P)s in case of A1 being NAD(P)s and B2 is an oxidized form of B1, and determining an amount of converted A2 or B1 by the said reaction, and a composition for assay of chiroinositol. Chiroinositol can be assayed by accurate, simple, low price and high sensitive method.

5 Claims, 6 Drawing Sheets pH DEPENDENCY

OTHER PUBLICATIONS

T. Niwa et al., "Identification of 6–deoxyallitol and 6–deoxygulitol in human urine Electron–impact mass spectra of eight isomers of 6–deoxyhexitol", *Journal of Chromatography,* vol. 336, 1984, pp. 345–350.

A. Weissbach, The Enzymic Determination of Myo–Inositol, *Biochimica et Biophysica Acta,* vol. 27, 1958, pp. 608–611.

P. Sneath, "Endospore–forming Gram–Positive Rods and Cocci",*Bergery's Manual of Systematic Bacteriology,* vol. 2, pp. 1104–1139.

M. Vidal–Leiria et al., "Inositol Dehydrogenase from the Yeast Cryptococcus Melibiosum", *Biochimica et Biophysica Acta,* vol. 293, 1973, pp. 295–303.

T. Berman et al., The Pathway of myo–Inositol Degradation in Aerobacter Aerogenes, *The Journal of Biological Chemistry,* vol. 241, No. 4, 1966, pp. 800–806.

FIG. 1 pH DEPENDENCY

FIG. 2

HEAT STABILITY

FIG. 3

OPTIMUM TEMP.

FIG. 4

CALIBRATION CURVE
(THIO-NAD/NADH)

HIGHLY SENSITIVE METHOD FOR ASSAYING CHIRO-INOSITOL AND COMPOSITIONS FOR THE ASSAY

FIELD OF THE INVENTION

This invention relates to high sensitive assay method of chiroinositol and a composition for assay thereof in fields of clinical biochemistry and food inspection. More particularly, this invention relates to an assay method of chiroinositol which comprises reacting a specimen containing chiroinositol with 1) a dehydrogenase, which catalyses at least reversible reaction with a substrate of chiroinositol in the presence of a coenzyme selected from nicotinamide adenine dinucleotides (phosphate) [hereinafter designates as NAD(P)s] and a coenzyme selected from thio-nicotinamide adenine dinucleotides (phosphate) [hereinafter designates as thio-NAD(P)s ]
2) A1 and
3) B1 to form cycling reaction of the formula wherein a product is a compound, from which 2 or 4 hydrogen atoms are deleted from chiroinositol, A1 is NAD(P)s or thio-NAD(P)s, A2 is a reduced form of A1, B1 is a reduced form of NAD(P)s in case of A1 being thio-NAD(P)s or a reduced form of thio-NAD(P)s in case of A1 being NAD(P)s and B2 is an oxidized form of B1, and determining an amount of converting A2 or B1 by the said reaction. The present invention further relates to a composition for assay of chiroinositol comprising consisting of following components 1)–3);

1) a dehydrogenase, which catalyses at least reversible reaction with a substrate of chiroinositol in the presence of a coenzyme selected from NAD(P)s and a coenzyme selected from thio-NAD(P)s,
2) at least a coenzyme selected from NAD(P)s and thio-NAD(P)s, and
3) in the above 2), at least a coenzyme selected from reduced thio-NAD (P)s in case of at least a coenzyme selected from NAD(P)s, or in the above 2), at least a coenzyme selected from reduced NAD(P)s in case of at least ,t coenzyme selected from thio-NAD(P)s.

PRIOR ARTS

In recent years, since an importance in insulin resistance has been recognized as a cause of glucose tolerance failure including diabetes mellitus, especially diabetes mellitus type II, or as a risk factor for arteriosclerosis, some of assay methods for insulin resistance have developed. However, idealistic assay methods with highly accuracy, simple and low price have never been known.

Involvement of chiroinositol in insulin signal has reported and is thought to be an index for insulin resistance. [Larner J. et al., New Eng. J. Med., 323, 373–378 (1990), Published Japanese translation of PCT international publication for patent application (hereinafter designates as JPCT) No. 4-504001 (WO90/10711) and JPCT No. 4-505218 (WO91/12335A)]. The above JPCT No. 4-504001 and JPCT No. 4-505218 disclose that assay of chiroinositol in body fluid such as blood or urine for diagonosis of diabetes mellitus, especially insulin resistance, is useful, and suggest reduction/oxidation analysis using enzyme, however no concrete method has proposed.

Chiroinositol measured by GC-mass spectrum analysis has been reported. [Toshimitsu Niwa, J. Chromatography, 227 (1983), 25–39, ibid, 336 (1984), 345–350]. These methods require, however, pretreatment with complex operation and difficult to treat for many specimens as well as require expensive equipment, which cause high costs.

In Japanese Unexamined Patent Publication No. 8-21835, immunoassay using specific antibody for chiroinositol is disclosed for solving these problems. There may be problems, however, in the immunochemical assay with highly sensitive in one hand and with less reproducibility, effective for treatment of specimens in a unit time and cost effectiveness as compared with biochemical assay method using enzyme in the other hand.

For supplying accurate, simple and low cost assay method for chiroinositol, enzymatic method may be one of the most preferable methods. However, there is no clear-cut report on an enzyme which catalyses a reaction with chiroinositol. Especially, no report is known on an enzyme which catalyses a reaction with chiroinositol using thio-NAD(P)s as coenzymes.

Myoinositol dehydrogenase produced by Aerobacter aerogenes has been reported to have very weak activity for chiroinositol in its substrate specificity using a coenzyme NAD as compared with myoinositol (Biochim. Biophys. Acta 17, 608, 1958). Consequently, such the enzyme may not be preferable for assay of chiroinositol, which is observed trace level in vivo. Commercially available myo-inositol dehydrogenase (originated from Aerobacter aerogenes, SIGMA Inc. I-0255) did not use thio-NAD(P)s as a coenzyme.

Further, there is a report that inositol dehydrogenase originated from *Cryptococcus melibiosum* catalyses a reaction with (+) inositol (Biochim. Biophys. Acta; 293, 295, 1973). We have cultured this strain, obtained crude enzyme and tried to make experiment and found that it can use NAD(P)s as a coenzyme but can not use thio-NAD(P)s. Consequently, the said enzyme can riot constitute cycling reaction with thio-NAD(P)s and NAD(P)s.

Problems to be solved by the invention

An object of the present invention is to provide a method for assay of chiroinositol with accurate, simple, low cost and high sensitive method using an enzyme which acts on chiroinositol and a composition for assay thereof.

Means for solving problems

In order to assay trace amount of chiroinositol in vivo in clinical biochemical test, not only direct assay method of reduced coenzyme using dehydrogenase but also a combination with coloring agent for assay is resulted to insufficient sensitivity. We have found that an enzyme originated from Bacillus sp. No. 3 has an activity for chiroinositol. A compound generated by an action of the enzyme derived from Bacillus sp. No. 3 on chiroinositol in the presence of NAD is, for example different from the case that myoinositol dehydrogenase derived from Aerobacter aerogenes acts on myoinositol in the presence of NAD to delete 2 hydrogen atoms to form myoinosose 2, under sufficient progressive condition for reaction, a compound generated from a reaction in which at first 2 hydrogen atoms are deleted, then 2 hydrogen atoms are further deleted. A spot of the said final compound can not detected by paper chromatography [J.

Biol. Chem., 241 (4); 1966, 800–806]. Since the said final compound is different from myoinosose 2 and is very unstable, to construct a stable enzymatic cycling reaction might be impossible.

We have studied for solving the problems in this point and surprisingly found that the enzyme derived from Bacillus sp. No. 3 catalyzed the reaction with chiroinositol as a substrate in the presence of coenzymes thio-NAD(P)s and NAD(P)s to construct the following cycling reaction;

wherein a product is a compound, from which 2 or 4 hydrogen atoms are deleted from chiroinisitol, A1 is NAD(P)s or thio-NAD(P)s, A2 is a reduced form of A1, B1 is a reduced form of NAD(P)s in case of A1 being thio-NAD(P)s or a reduced form of thio-NAD(P)s in case of A1 being NAD(P)s and B2 is an oxidized form of B1, and can be used for assay, with high sensitivity, of chiroinositol existing in vivo by assaying increased amount of thio-NAD(P)H or decreased amount of NAD(P)H. Further we have found that thio-NAD(P) can be replaced by NAD(P) as well as replacing NAD(P)H by thio-NAD(P))H. Thereby the present invention has completed.

The present invention relates to an assay method of chiroinositol which comprises reacting a specimen containing chiroinositol with
1) a dehydrogenase, which catalyses at least reversible reaction with a substrate of chiroinositol in the presence of a coenzyme selected from nicotinamicle adenine dinucleotides (phosphate) [hereinafter designates as NAD(P)s] and a coenzyme selected from thio-nicotinamide adenine dinucleotides (phosphate) [hereinafter designates as thio-NAD(P)s ],
2) A1 and
3) B1
to form cycling reaction of the formula wherein a product is a compound, from which 2 or 4 hydrogen atoms are deleted from chiroinositol, A1 is NAD(P)s or thio-NAD(P)s, A2 is a reduced form of A1, B1 is a reduced form of NAD(P)s in case of A1 being thio-NAD(P)s or a reduced form of thio-NAD(P)s in case of A1 being NAD(P)s and B2 is an oxidized form of B1, and determining an amount of converting A2 or B1 by the said reaction. The present invention further relates to a composition for assay of chiroinositol comprising consisting of following components 1)–3);
1) a dehydrogenase, which catalyses at least reversible reaction with a substrate of chiroinositol in the presence of a coenzyme selected from nicotinamide adenine dinucleotides (phosphate) [hereinafter designates as NAD(P)s] and a coenzyme selected from thio-nicotinamide adenine dinucleotides (phosphate) [hereinafter designates as thio-NAD(P)s],
2) at least a coenzyme selected from NAD(P)s and thio-NAD(P)s, and
3) in the above 2), at least a coenzyme selected from reduced thio-NAD(P)s in case of at least a coenzyme selected from NAD(P)s, or in the above 2), at least a coenzyme selected from reduced NAD(P)s in case of at least a coenzyme selected from thio-NAD(P)s.

Preferable constituents and embodiments of the present invention are explained in details hereinbelow.

An enzyme used in the present invention can be any of a dehydrogenase, which catalyses at least reversible reaction with a substrate of chiroinositol in the presence of at least a coenzyme selected from NAD(P)s and at least a coenzyme selected from thio-NAD(P)s. The enzyme can be selected by confirming the enzyme reaction using a substrate chiroinositol and coenzymes consisting of a coenzyme selected from NAD(P)s and a coenzyme selected from thio-NAD(P)s. Example of enzyme is an enzyme produced by Bacillus sp. No. 3 belonging to genus Bacillus.

The present enzyme is a specific enzyme which can act on chiroinositol and can be used coenzymes of NADs, NADPs, thio-NADs and thio-NADPs. The enzyme is preferably used for high sensitive assay by applying enzymatic cycling using thio-NAD(P)s and NAD(P)s.

The present strain Bacillus sp. No. 3 has been deposited in the National Institute of Bioscience and Human-Technology,Agency of Industrial Science and Technology, Ministry of International Trade and Industry, in Higashi 1-1-3, Tsukuba-shi, Ibaragi-ken, Japan on Mar. 19, 1997 as FERM BP-5881. Taxonomical properties of the strain are illustrated hereinbelow.

(a) Morphological properties

Straight or slightly curved bacilli with round edges, size of 0.5–0.7×1.5–3.5 μm with peritrichous movement. Elliptical to oviform sporulation with 0.8×1.0–2.0 μm in edge or subedge and expanded by sporulation. No polymorphism.

(b) Growth condition in various media

Observed findings on various media cultured at 50–52° C. for 1–2 days are as follows.

1) Nutrient agar plat medium

Forms round with convex colonies. Smooth and round edge surface. Ocher to plae ocher in color. No formation of soluble pigment.

2) Nutrient agar slant medium

Cottony good growth. Ocher to pale ocher in color. No formation of soluble pigment.

3) Liquid medium (peptone water)

Good growth with uniform turbid.

4) Ltmus milk medium

Weakly acidic after 4–5 days.

(c) Physiological and biochemical properties [+: positive, +: weakly positive, −: negative, NT: not tested]

| | |
|---|---|
| GC molar ratio % : 41.9% (HPLC) | |
| Major isoprenoid quinone : MK-7 | |
| Gram's stain | + |
| KOH reaction | − |
| Capsule formation | − |
| Acid-fast stain | − |
| OF test (Hugh-Leifson) | NT |
| OF test (nitrogen source : $NH_4H_2PO_4$) | F |
| Aerobic growth | + |
| Anaerobic growth | + |
| Growth temperature at 70° C. | − |
| 60° C. | + |
| 37° C. | + |
| 30° C. | − |
| Halotolerant 0% | + |
| 3% | + |
| 5% | − |
| Growth pH 5.6 | |

-continued

| | |
|---|---|
| 6.2 | − |
| 9.0 | + |
| Gelatin hydrolysis | + |
| Starch hydrolysis | (+) |
| Casein hydrolysis | − |
| Esculin hydrolysis | + |
| Tyrosine hydrolysis | − |
| Arginine hydrolysis | − |
| Cellulose hydrolysis | − |
| Catalase production | + |
| Oxidase production | + |
| Lecithinase production | − |
| Urease production (SSR) | − |
| Urease production (Chris) | − |
| Indole production | − |
| H₂S production (detected by lead acetate paper) | − |
| Acetoin production (K₂HPO₄) | − |
| Acetoin Production (NaCl) | − |
| MR test | − |
| Nitrate reduction test (gas formation) | − |
| (NO₂ - detection) | − |
| (NO₃ - detection) | + |
| Utilization on Simmons medium | |
| Citrate | − |
| Malate | − |
| Maleate | − |
| Malonate | − |
| Propionate | − |
| Gluconate | − |
| Succinate | − |
| Utilization on Christensen medium | |
| Citrate | + |
| Malate | − |
| Maleate | − |
| Malonate | − |
| Propionate | + |
| Gluconate | − |
| Succinate | − |
| Gas formation from glucose | − |
| Acid formation from various sugars | |
| Adnitol | − |
| L (+) arabinose | − |
| Cellobiose | + |
| Dulcitol | − |
| Meso-erythritol | − |
| Fructose | + |
| Fucose | + |
| Galactose | + |
| Glucose | + |
| Glycerin | + |
| Inositol | + |
| Inulin | + |
| Lactose | + |
| Maltose | + |
| Mannitol | + |
| Mannose | + |
| Melezitose | − |
| Melibiose | + |
| Raffinose | − |
| Rhamnose | + |
| D-ribose | + |
| Salicin | + |
| L-sorbose | − |
| Sorbitol | − |
| Starch | + |
| Saccharose | + |
| Trehalose | + |
| Xylose | − |

As shown in the above, major properties of the present strain is a bacilli with Gram (+) bacterium, size in 0.5–0.7× 1.5–3.5 μm with peritrichous movement, with sporulation, no polymorphism, fermentative decomposition of glucose and acid production. Catalase and oxidase formation positive. Thermophilic facultative anaerobic. From these characteristics, the present strain is referred to genus Bacillus.

Species of this strain in Bacillus is identified as follows. According to Bergey's Manual of Systematic Bacteriology, Vol. 2, Bacillus species, which grow at high temperature (at 50° C.), are known 9 species of *B. acidocaldarius, B. subtilis, B. badius, B. brevis, B. coagulans, B. licheniformis, B. petntothenticus, B. schegelli* and *B. stearothermophilus*. Among them, the species which grow under anaerobic condition are only known two species, i. e. coagulans (hereinafter sometimes designates as "C") and *B. licheniformis* (hereinafter sometimes designates as "L"). Comparison with taxonomical properties of C, L and the present strain are shown as follows.

In the table; +: positive, (+): weakly positive, −: negative, d: differ in the strain, ND: no data.

| | C | L | the Present Strain |
|---|---|---|---|
| Oxidase production | − | d | + |
| Expansion with spore | d | − | + |
| Anaerobic growth | + | + | + |
| Acetoin production | + | + | − |
| Glucose (acid) | + | + | + |
| L-arabinose (acid) | + | + | + |
| Xylose | d | + | − |
| Mannitol (acid) | d | + | + |
| Casein hydrolysis | d | + | − |
| Gelatin hydrolysis | d | + | − |
| Starch hydrolysis | − | + | (+) |
| Citrate utilization | + | + | − |
| Propionate utilization | d | + | − |
| Tylosine hydrolysis | − | + | − |
| LV reaction | − | + | − |
| Indole production | − | + | − |
| Halotolerance 2 % | + | + | + |
| 5% | − | + | − |
| 7% | − | + | − |
| 10% | − | ND | − |
| Growth temp. 40° C. | + | + | + |
| 50° C. | + | + | + |
| 55° C. | + | + | + |
| 60° C. | ND | ND | − |
| 70° C. | − | − | + |
| Nitrate reduction | d | + | − |
| GC mole % of DNA | 44.5 (Type) 44.3~50.3 | 46.4 (Type) 42.9~49.9 | 41.9 |

As a result of the above comparison, the properties of the present strain is similar to those of *Bacillus coagulans*, however properties on acetoin production, GC molar ratio of DNA, and a reaction on litmus milk, though not to mention in the table, are different from properties. Consequently, the present strain is referred to Bacillus sp. No. 3 in order to differentiate from the known Bacillus species.

Further, we have found that an enzyme produced by microorganism strains such as *Streptomyces roseogriseus* 301 belonging to genus Streptomyces and *Agrobacterium rhizogenes* 1215 belonging to genus Agrobacterium has an action on chiroinositol with coenzyme NAD(P)s and thio-NAD(P)s, and can be used for high sensitive assay by applying with enzyme cycling using NAD(P)s and thio-NAD(P)s.

*Streptomyces roseogriseus* 301 has been deposited in the National Institute of Biosceience and Human-Technology, Agency of Industrial Science and Technology, Ministry of International Trade and Industry, in Higashi 1-1-3, Tsukuba-shi, Ibaragi-ken, Japan on Feb. 26, 1998 as FERM BP-6269. *Agrobacterium rhizogenes* 1215 culture collection strains list No. MAFF 301726 of the National Institute of Agrobiological Resources, in Kannondai 2-1-2, Tsukuba-shi, Ibaragi-ken, Japan, and has been deposited in the National Institute of Bioscience and Human-Technology, Agency of Industrial Science and Technology, Ministry of International Trade and Industry, in Higashi 1-1-3, Tsukuba-shi, Ibaragi-ken, Japan on Feb. 26, 1998 as FERM BP-6270. Taxonomical properties of *Streptomyces roseogriseus* 301 are shown as follows.

| Test items | Result |
|---|---|
| (a) Cell wall type | Type I |
| LL-diaminopimeric acid | + |
| Meso-diaminopimeric acid | − |
| Diamino butyric acid | − |
| Glycine | + |
| Aspartic acid | − |
| Ornitine | − |
| Lysine | − |
| Arabinose*[1] | − |
| Galactose*[1] | − |
| (b) Quinones | MK-9 (H6), −9 (H8), −9 (H4) |
| (c) Substrate mycelia | + |
| (d) Aerial mycelia | + |
| (e) Spore chain form | RF *[2] |
| (f) Color of colony surface | gray series |
| (g) Melanin pigment formation | + |
| (h) Assimilation of carbon sources | |
| Arabinose | + |
| Xylose | + |
| Inositol | + |
| Mannitol | + |
| Lactose | + |
| Rhamnose | + |
| Sucrose | + |
| Raffinose | + |

*[1]Estimated by using sulfuric acid hydrolysate of whole cells.
*[2]RF; rectiflexibiles (straight-curve-wavy)

The present strain has cell wall type 1, and from the nature of quinone system and a form of spore chain, it is estimated as a strain belonging to genus Streptomyces. Further this strain is estimated to belong *Streptomyces roseogriseus* or *Streptomyces actuosus*. Consequently, the present strain is compared with its properties to those of type strains of *Streptomyces roseogriseus* IFO 13406 and *Streptomyces actuosus* IFO 13009. Results indicate that the present strain is referred to *Streptomyces roseogriseus* due to similarity of spore chain length of *Streptomyces roseogriseus*. The present strain is referred to *Streptomyces roseogriseus* 301 and deposited as FERM BP-6269.

Pure enzyme can be obtained by culturing the above Bacillus sp. No. 3, *Streptomyces roseogriseus* 301 or *Agrobacterium rhizogenes* 1215, and applying known isolation and purification methods of proteins and enzymes. Producing microorganisms used in the present invention can be the above mentioned Bacillus sp. No. 3, *Streptomyces roseogriseus* 301 or *Agrobacterium rhizogenes* 1215. Since the nature of bacteria can easily be mutated in their taxonomical properties, artificial mutants, which can be prepared by artificial mutation means such as naturally or commonly performed ultraviolet irradiation, radiation or treatment with mutant inducer such as N-methyl-N'-nitro-N-nitrosoguanidine or ethyl methanesulfonate, and natural mutants can be used, if such strains have ability to produce dehydrogenase having activity for reversible reaction with a substrate of chiroinositol (hereinafter sometimes designates as dehydrogenase for chiroinositol) as well as belonging to genus Bacillus, genus Streptomyces or genus Agrobacterium, in the present invention. Further transformed bacteria, to which a gene expressing enzyme acting on chiroinositol can also be used in the present invention.

The above cultivation can be performed by applying conditions used in the common culture of bacteria. Media used are nutrient media containing assimilable carbon sources for microorganisms, digestible nitrogen sources, and if necessary inorganic sources. Examples of assimilable carbon sources are glucose, fructose, saccharose or inositol, in a single or in combination. Examples of digestible nitrogen sources are peptone, meat extracts or yeast extracts, in a single or in combination. Further, salts such as phosphate, magnesium salt, calcium salt, potassium salt, sodium salt, and other heavy metal salts such as iron or manganese can also be used, if necessary. Among others, known assimilable carbon sources and digestible nitrogen sources can also be used.

Culture process can be performed, in general, preferably by shake culture or aeration stirring culture under aerobic condition. For industrial purpose, submerged aeration culture is preferable. Culturing temperature may be altered under conditions for growing dehydrogenase, which acts on chiroinositol, producing bacteria and producing the enzyme used in the present invention. Generally, it is preferable at 20–60° C., specifically approximately at 50° C. for Bacillus sp. No. 3 and at 30° C. for *Agrobacterium rhizogenes* 1215 and *Streptomyces roseogriseus* 301. Culturing time can be different in the culture conditions, and the cultivation can be performed when the enzyme production reaches its maximum potency. In general, it is about 1–2 days. Conditions of medium such as composition of medium, liquid nature of medium, culturing temperature, stirring speed and aeration condition can be adjusted and selected in order to obtain preferable result for production. In case of foaming in the liquid culture, anti-foam agents such as silicon oil and vegetable oil can be used.

The thus obtained dehydrogenase, which has activity for chiroinositol, is an intracellular enzyme, and the cultured cells are collected by filtration or centrifugation from the cultured mass. The cells are treated with combination of microbial cell treatment means, for example mechanical disruption such as by sonication, French press, glass beads or lyophilization, or enzymatic lysis such as lysozyme, to obtain crude dehydrogenase solution having activity for chiroinositol.

Purification can be performed by combining with salting-out such as using ammonium sulfate or sodium sulfate, chromatography such as using molecular sieve or ion exchange resins, electrophoresis, ultracentrifugation, desalting, heating or chemical means. Examples of chromatography are cation or anion exchange chromatography, gel-permeation chromatography, partition chromatography, absorption chromatography, normal phase chromatography, reverse phase chromatography, hydrophobic chromatography, hydroxyapatite chromatography or affinity chromatography. Purified enzyme can be stored in the liquid state or lyophilized state under cooling or freezing. Stabilized agents for enzyme solution or lyophilization can also be added. Examples of stabilizing agents are sugars such as mannitol, saccharose and sorbitol, amino acid such as glutamic acid and glycine, and peptide O)r protein such as albumin.

Properties of enzyme which catalyses chiroinositol originated from Bacillus sp. No. 3 are as follows.

(1) Assay method for dehydrogenase activity for chiroinositol (1)-1 Composition of reaction solution

| | |
|---|---|
| 100 mM | Tris-HCl buffer pH 8.5 |
| 20 mM | D-chiroinositol (Wako Pure Chemicals Inc. Japan) |
| 2 mM | NAD (Oriental Yeast Corp. Japan) |
| 5 U/ml | Diaphorase (Asahi Kasei Kogyo K.K., Japan) |
| 0.025 % | NBT (Wako Pure Chemicals Inc., Japan) |
| 1.5 % | Triton-X 100 (Wako Pure Chemicals Inc., Japan) |

(1)-2 Assay of enzyme activity

The above reaction mixture 1 ml in a test tube is incubated at 37° C. for 5 minutes. Diluted enzyme solution 20 μl is added and stirred to initiate reaction. After exactly 5 minutes, the reaction is terminated by adding 0.1N HCl, 2 ml and stirred. A1 is obtained by measuring A550. Simultaneously, the above reaction mixture without addition of chiroinositol is incubated by the same manner to obtain optical absorption A0. Enzyme activity is measured by the following equation.

$$U/ml = \frac{(A1-A0)}{18.3} \times \frac{1}{5} \times \frac{3.02}{0.02} \times B$$

B: dilution rate 18.3: molecular absorption coefficient of NBT

5: reaction time 3.02: total reaction value (ml)

0.02: amount of enzyme solution (ml)

(2) Enzyme reaction

The present enzyme catalyses a reaction for generating reduced coenzyme [NAD(P)Hs and thio-NAD(P)Hs] in the presence of chiroinositol and coenzyme [NAD(P)s and thio-NAD(P)s]. Examples of the above NAD(P)s are nicotinamide adenine dinucleotide (NAD), acetylpyridine adenine dinucleotide (acetyl NAD), nicotinamide hypoxanthine dinucleotide (deamino NAD), pyridine aldehyde adenine dinucleotide (aldehyde NAD), pyridine aldehyde hypoxanthine dinucleotide (aldehydedeamino NAD) and phosphate thereof.

Examples of the above thio-NAD(P)s are thio-nicotinamide adenine dinucleotide (thio-NAD) and thio-nicotinamide hypoxanthine dinucleotide (thio-deamino NAD) arid phosphate thereof. Initial rate of enzyme reaction (originated from Bacillus sp. No. 3) are: NAD; 13 Abs/min., acetyl NAD; 260 mAbs/min., deamino NAD; 12 Abs/min., aldehyde NAD; 140 mAbs/min., NADP; 80 mAbs/min. and thio-NAD; 2.5 Abs/min.

Composition of reaction solution

| | |
|---|---|
| 100 mM | Gly-NaOH buffer approx. pH 10 (at optimum pH) |
| 10 mM | D-chiroinositol (Wako Pure Chemicals Inc., Japan) |
| 1 mM | Coenzyme (NAD(P), thio-NAD(P); Oriental Yeast Corp., Japan, acetyl-, aldehyde-, deamino-NAD; Sigma Corp., U.S.A.) |

Optimum pH are pH 11.0 for NAD, deamino NAD and thio-NAD, pH 10.5 for acetyl NAD, and pH 10.0 for aldehyde NAD and NADP.

The above reaction solution 1 ml in quartz cell is set in spectrophotometer which is controlled at 37° C. After over 5 minutes incubation, enzyme solution 140 U/ml (NAD and deamino NAD; 14 U/ml) 20 μl is added and stirred. Absorption changes per minute in specific wavelength for each reduced coenzyme is measured to obtain initial reaction rate. (For NAD and deamino NAD, measured value is increased number by ten for adjusting the amount of enzyme.)

A product in the present cycling reaction is an amount of reduced NAD generated by the reaction with chiroinositol and excess amount of NAD. In the reaction, 2 hydrogen atoms are deleted at the first reaction and 2 hydrogen atoms are further deleted at the second reaction. These are confirmed by increase in reduced NAD, which is determined by an amount of formazan pigment having maximum absorption at 550 nm generated as a result of an act on of NBT (nitroblue tetrazolium) on the reduced NAD in the presence of diaphorase.

(3) Molecular weight 135,000+10,000

Determined by gel filtration using HPLC. Column: TSK gel G3000SW (7.50×600 mm; Toso Corp., Japan), eluate; 50 mM phosphate buffer (pH 7.0)+0.3 M NaCl, molecular marker; Oriental Yeast Corp., Japan. Chromatography equipment: Shimadzu Corp., Japan.

(4) Isoelectric point pH 4.7±0.5

Focusing electrophoresis using carrier ampholites, at 4° C., constant voltage at 700 V for 40 hours. After fractionation, activity of each fraction is measured.

(5) Optimum pH

Approx. pH 11

Figure 1:
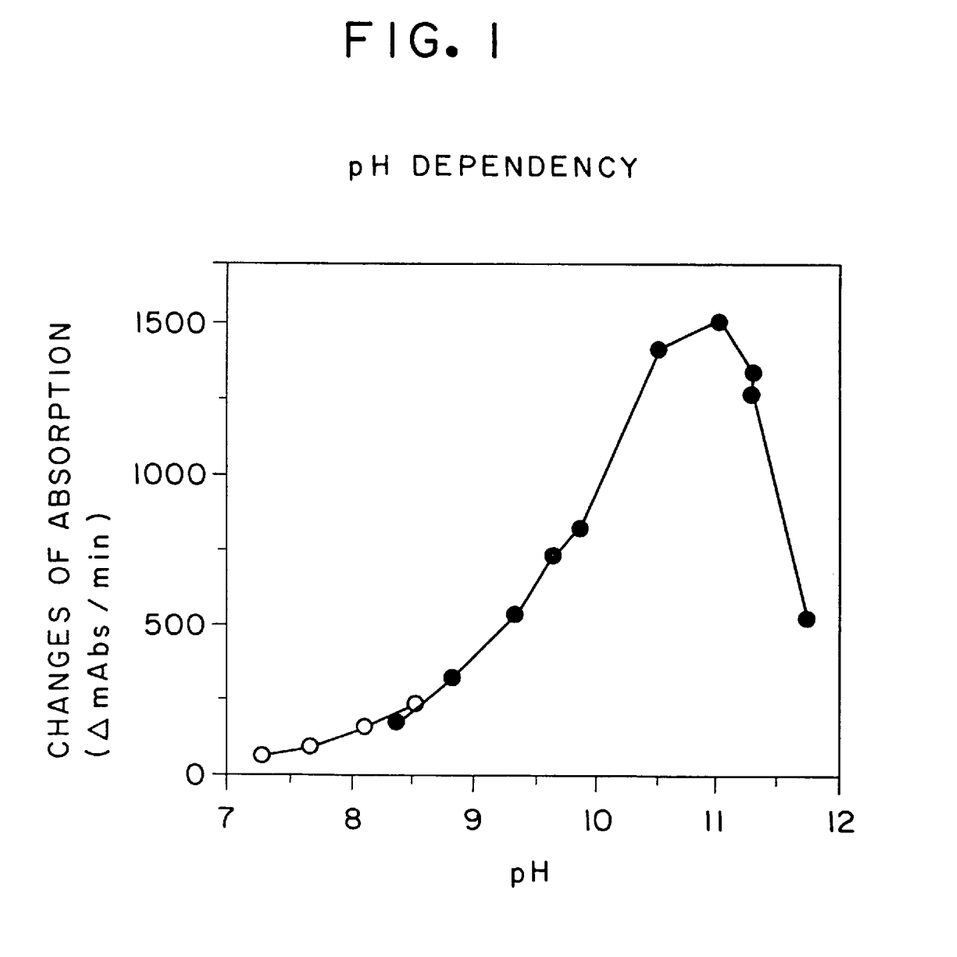
FIG. 1 shows curve of pH dependency of the enzyme produced by Bacillus sp. No. 3 which catalyses chiroinositol using coenzyme NAD.

Relative activity assay method hereinbelow is applied. 100 mM glycine buffer, pH 11.0 in the reaction solution is replaced by 100 mM Tris buffer (pH 7.5–9.0, -○-) and 100 mM glycine buffer (pH 8.5– 11.8, -●-). FIG. 1 shows relative activity of enzyme derived from Bacillus sp. No. 3 in each pH, and at pH 11, maximum activity is observed.

Assay method for relative activity:

Composition of reaction solution

| | |
|---|---|
| 100 mM | glycine-NaOH buffer (pH 11.0) |
| 1 mM | NAD (Oriental Yeast Corp., Japan) |
| 10 mM | D-chiroinosiol (Wako Pure Chemicals Inc., Japan) |

The above reaction solution 1 ml in quartz cell is set in spectrophotometer which is (controlled at 37° C. After over 5 minutes incubation, aliquot diluted enzyme solution 20 μl is added and stirred. Absorption changes per minute at $A_{340}$ are measured to obtain initial reaction rate and to calculate relative activity.

(6) Heat stability

Figure 2:
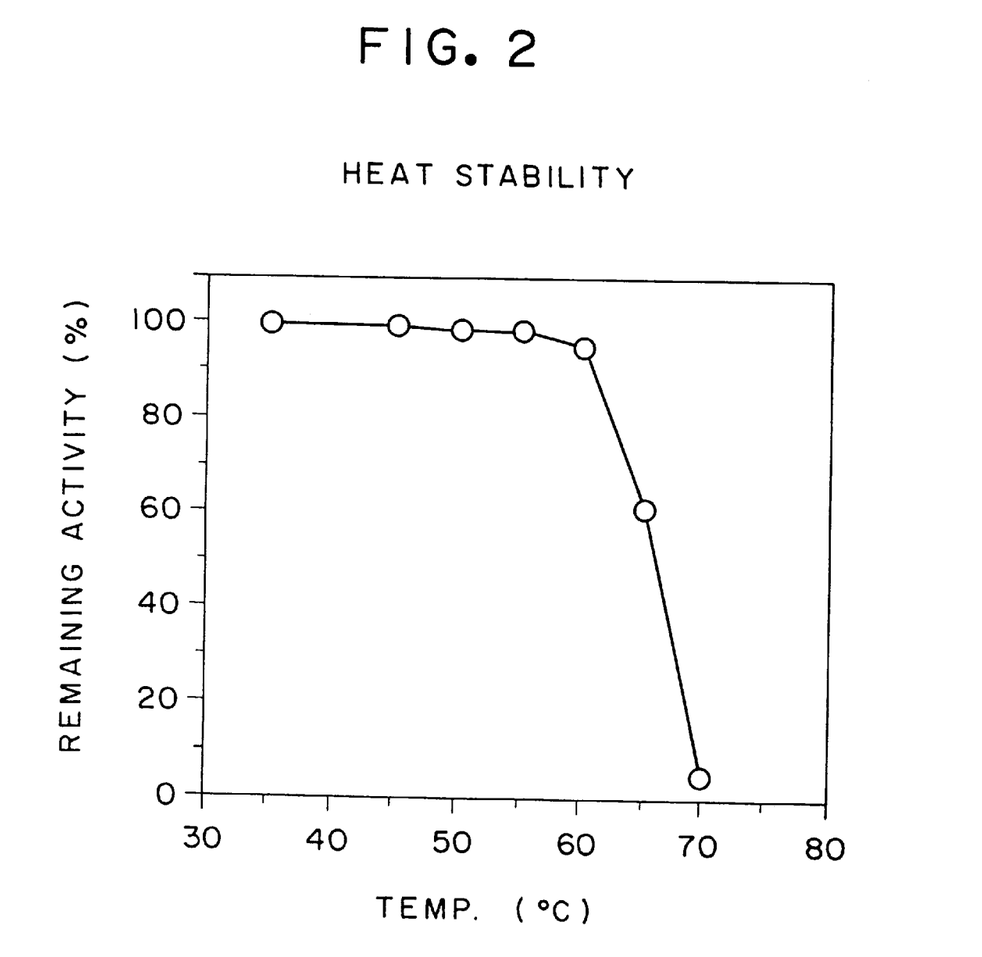
FIG. 2 shows curve of heat stability of the enzyme produced by Bacillus sp. No. 3 which catalyses chiroinositol using coenzyme NAD.

Enzyme solution (1 U/ml) is heat treated in 20 mM phosphate buffer (pH 7.0) for 15 minutes. Remained activity is measured by the method of assay hereinabove. FIG. 2 shows remained activities treated at various temperatures. Result indicates that approximately 100% activity is 55° C.

(7) Optimum temperature

Figure 3:
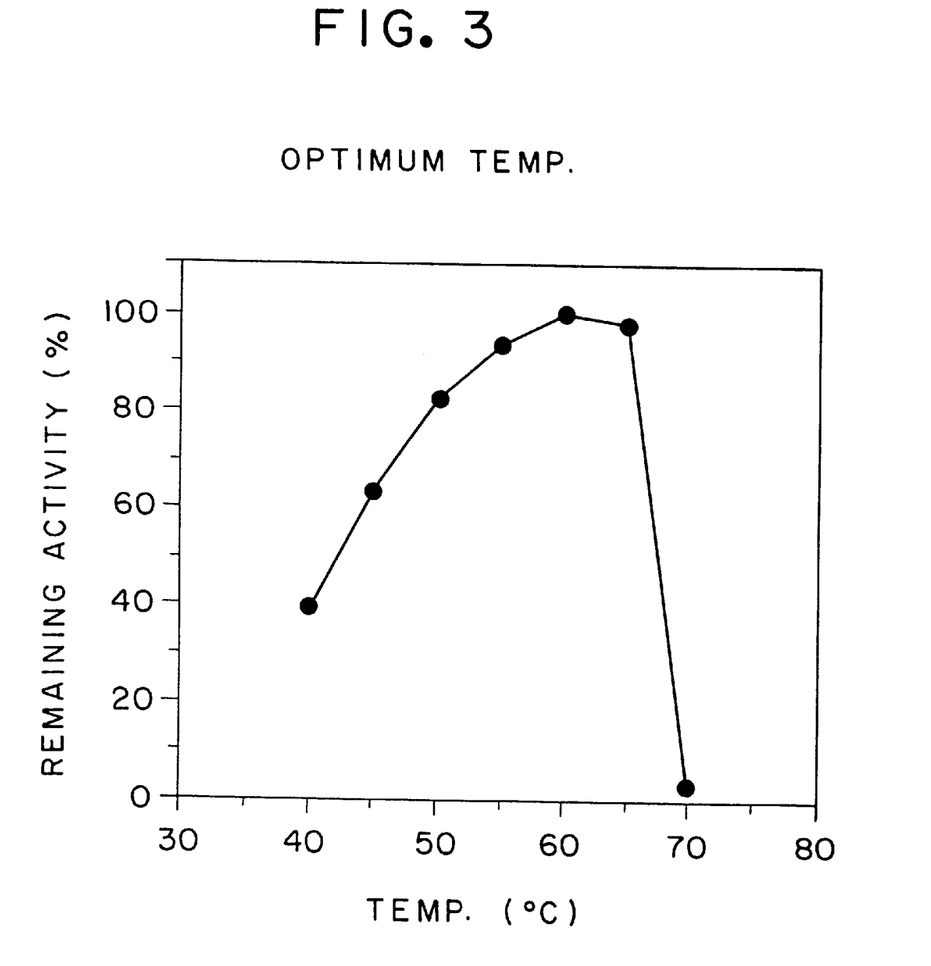
FIG. 3 shows curve of optimum temperature of the enzyme produced by Bacillus sp. No, 3 which catalyses chiroinositol using coenzyme NAD.

Enzyme activities at 40–70° C. are assayed according to a method hereinabove using 100 mM Tris-HCl bufer (pH 8.5). As shown in FIG. 3, maximum activity is observed at 60° C.

(8) Km value

Km values are measured at various concentrations using 10 mM D-chiroinositol and mM NAD.

Km for D-chiroinositol 5.2±0.5 mM

Km for NAD: 0.5±0.1 mM

Km for thio-NAD is measured by replacing NAD to thio-NAD.

Km for D-chiroinositol: 12.8±0.5 mM

Km for thio-NAD: 0.9±0.1 mM

As shown in the above, the present enzyme utilizes not only NAD but also thio-NAD as a coenzyme, and is specific enzyme having stable reactivity for chiroinositol.

(9) Substrate specificity

Substrate specificity of the present enzyme is shown in Table 1.

TABLE 1

| Substrate | Relative activity |
|---|---|
| chiroinositol | 100% |
| myoinositol | 9% |
| scylloinositol | 0% |
| epi-inositol | 0% |
| galactose | 0% |
| fructose | 0% |
| mannose | 0% |
| mannitol | 0% |

Substrate specificity is assayed by using following reaction solution at the equal concentration of substrates.

Composition of reaction solution

| 200 mM | glycine-NaOH buffer (pH 9.8) |
|---|---|
| 0.03 mM | NADH (Oriental Yeast Corp., Japan) |
| 100 U/ml | dehydrogenase which catalyses chiroinosiol (Originated from *Bacillus sp.* No. 3) |
| 2 Mm | thio-NAD (Oriental Yeast Corp., Japan) |

D-chiroinositol, galactose, fructose, mannitol, mannose; Japan, Wako Pure Chemicals Inc., myo-, epi-, scyllo-inositol U.S.A. SIGMA Corp.

Properties of crude enzymes which catalyses chiroinositol produced by *Agrobacterium rhizogenes* 1215 (hereinafter sometimes designates as A. r. 1215) and *Streptomyces roseogriseus* 301 (hereinafter sometimes designates as S. r. 301) are shown as follows.

(1) Enzyme assay method

The same as in the enzyme originated from Bacillus sp. No. 3.

(2) Enzyme action

The same as in the enzyme originated from Bacillus sp. No. 3. Relative activities using various coenzymes are shown in Table 2 (activity using NAD is set as 100%).

TABLE 2

| | A.r.1215 origin | S.r.301 origin |
|---|---|---|
| NAD | 190% | 100% |
| NADP | 1855% | 0% |
| acetyl-NAD | 26% | 195% |
| aldehyde-NAD | 15% | 20% |
| deamino-NAD | 44% | 110% |
| thio-NAD | 0% | 6% |
| thio-NADP | 269% | 0% |

| 3) Molecular weight | |
|---|---|
| A. r. 1215 origin | 100,000 ± 10,000 |
| S. r. 301 origin | 100,000 ± 10,000 |

Measured by the same method as in the enzyme originated from Bacillus sp. No. 3. Elution time of enzyme is determined by measuring absorption of UV at 280 nm and activities in each fraction.

| (4) Optimum pH | |
|---|---|
| A. r. 1215 origin | approx. pH 9 |
| S. r. 301 origin | approx. pH 9 |

(5) Heat stability

Measured by the same method as in the enzyme originated from Bacillus sp. No. 3.
A. r. 1215 origin: Remaining activity 100% by treatment at 40° C. for 15 minutes.
S. r. 301 origin Remaining activity 100% by treatment at 50° C. for 15 minutes.

(6) Km value

Km value for D-chiroinositol is shown. Measurement is performed by changing substrate concentration in the above assay method.
A. r. 1215 origin: 30.6±1.0 mM
S. r. 301 origin: 27.6±1.0 mM (7) Substrate specificity

Substrate specificity is shown in Table 3.

TABLE 3

| | A.r.1215 origin | S.r.301 origin |
|---|---|---|
| chiroinositol | 100% | 100% |
| myoinositol | 33% | 0% |
| scylloinositol | 0% | 0% |
| epi-inositol | 0% | 4% |
| fructose | 0% | 0% |
| mannose | 10% | 0% |
| mannitol | 0% | 0% |

In A. r. 1215 origin, the same assay method used in Bacillus sp. No. 3 is applied by replacing coenzyme to thio-NADP. In S. r. 301 origin, the reaction solution used for enzyme assay is used by replacing D-chiroinositol for various concentrations of substrates with adding constant concentration of enzyme solution to assay relative activities.

In order to assay extremely low concentration of chiroinositol in vivo, the enzyme cycling method shown by the following equation can generally be used.

wherein a product is a compound, from which 2 or 4 hydrogen atoms are deleted from chiroinositol, A1 and B2 are NAD(P)s or thio-NAD(P)s, A1 and B1 are reduced form thereof, and in A1 and B1, when A1 is thio-NAD(P)s, B1 is NAD(P)Hs, and when B1 is thio-NAD(P)H, A1 is NAD(P).

In case that dehydrogenase which catalyses chiroinositol used in an assay is required coenzyme of thio-NADs and NADs, the aforesaid thio-NADs and NADs can be selected, and in case that dehydrogenase which catalyses chiroinositol used in an assay is required coenzyme of thio-NADPs and NADPs, the aforesaid thio-NADPs and NADPs can be selected.

Amount of A1 and B1 requires excess as compared with amount of chiroinositol in the specimen, and also requires excess as compared with Km value for A1 and B1 of dehydrogenase for chiroinositol. In a composition for assay of chiroinositol used in cycling reaction of the present invention, concentration of A1 and B1 is 0.02–100 mM, preferably 0.05–50 mM. Amount of enzyme which catalyses chiroinositol is 1–1000 U/ml, preferably 5–500 U/ml. Amount thereof can be determined preferably depending on type and amount of specimens, consequently, the above levels are subject to change.

In case of enzyme cycling method in the present invention, if A1 and B1 are expensive, in order to reduce amount of A1 and B1, a combination of a dehydrogenase which constitutes a reaction of B2→B1 and not reacted with chiroinositol or a dehydrogenase which constitutes a reaction of A2→A1 and not reacted with chiroinositol and substrate for dehydrogenase can be used for reducing amount of A1 and B1.

For preparation of a composition for assay of chiroinositol of the present invention, enzyme used for acting on chiroinositol can be a dehydrogenase which uses coenzyme NAD(P)s, preferably NAD(P), and thio-NAD(P)s, preferably thio-NAD(P), and can be a dehydrogenase for assaying chiroinositol with high sensitivity by using enzyme cycling reaction. These can be confirmed by using these coenzymes and substrate based on the knowledge of the present invention.

A composition for assay can be prepared by selecting two or more coenzymes by considering Km value dehydrogenase for chiroinositol on each coenzyme, and setting a condition for reaction with adjusting pH within optimum pH between normal reaction and reverse reaction of the enzyme cycling for effective progress of the reaction. In case of dehydrogenase which catalyses chiroinositol from Bacillus sp. No. 3, Km values for NAD and thio-NAD are small as 0.50 mM and 0.87 mM, respectiviely, cosequently thio-NAD and NAD can be selected as coenzymes. In the cycling reaction, optimum pH of a reaction using thio-NAD is approximately pH 10.5, and that of the revrese reaction using NADH is approximately pH 10.0, consequently cycling can preferably be performed by selecting coenzymes of thio-NAD and NADH at approx. pH 10.

Examples of buff(er solution used are: buffer of pH 8–11 of organic amine buffer such as diethanolamine buffer, 2-ethylamino ethanol buffer, 2-amino-2-methyl-1-propanol buffer and N-methyl-D-glucamine buffer, at 20 mM–2 M, preferably 20 mM–1 M, most preferably 20 mM–500 mM, Good's buffer such as MES [2-(N-Morphilino) ethanesulfonic acid ] buffer, Bis-Tris [Bis(2-hydroxyethyl) iminotris (hydroxymethyl)methane ] buffer, ADA [N-(2-Acetamido)iminodiacetic acid ] buffer, PIPES [Piperazine-N, N'-bis(2-ethanesulfonic acid)] buffer, ACES [N-(2-Acetamido)-2 -aminoethanesulfonic acid] buffer, MOPSO [3-(N-Morpholino)-2-hydroxypropanesulfonic acid ] buffer, BES [N, N-Bis(2-hydroxyethyl)-2-aminoethanesulfonic acid] buffer, MOPS [3-(N-Morpholino)propanesulfonic acid] buffer, TES [N-Tris(hydroxymethyl)methyl-2-aminoethanesulfonic acid] buffer, HEPES [N-2-hydroxyethylpiperazine-N'-2-ethanesulfonic acid ] buffer, DIPSO {3- [N,N-Bis(2-hydroxyethyl)amino]-2-hydroxypropanesulfonic acid} buffer, TAPSO [N-Tris (hydroxymethyl)methyl-2-hydroxy-3-aminopropanesulfonic acid ] buffer, POPSO [Piperazine-N, N'-bis (2-hydroxypropanesulfonic acid ] buffer, HEPPSO [N-2-hydroxyethylpiperazine-N-hydroxypropane-3-sulfonic acid] buffer, EPPS [N-2-hydroxyethylpiperazine-N'-3-propanesulfonic acid] buffer, Tricine [Tris (hydroxymethyl) methylglycine ] buffer, Bicine [N,N-Bis(2-hydroxyethyl) glycine] buffer, TAPS [N-Tris (hydroxymethyl)methyl-3-aminopropanesulfonic acid] buffer, CHES [2-(Cyclohexylamino)ethanesulfonic acid] buffer, CAPSO [3-N-Cyclohexylamino-2-hydroxypropanesulfonic acid ] buffer and CAPS [3-Cyclohexylaminopropanesulfonic acid ] buffer at 20 mM–1 M, preferably 20 mM–500 mM, most prederably 20 mM–300 mM, and buffers for biochemical use such as glycine-NaOH, potassium hydrogen phosphate-sodium dihydrogen phosphate, HCl-sodium veronal-sodium acetate, potassium hydrogen phosphate-NaOH, HCl-Tris-amino methane, HCl-amino methylpropnae diol, ammonium chloride-ammonium, borate-NaOH, HCl-sodium dimethylglycine, glycine-NaCl-HCl, disodium citrate-HCl, and sodium veronal-sodium acetate, at 20 mM–1 M, preferably 20 mM–500 mM, most preferably 20 mM–300 mM. In case of using alkaline buffer, in order to make stable pH of buffer in free system, soluble hydrogen carbonate, which can release hydrogen carbonate ion such as ,;odium hydrogen carbonate, potassium hydrogen carbonate, magnesium hydrogen carbonate or calcium hydrogen carbonate, can be added at 10–500 mM, preferably at 50–200 mM for adjust pH. Enzyme used in these systems, single enzyme or combination of enzyme can be used.

Chiroinositol in specimens can be assayed using a composition for assaying chiroinositol of the present invention by adding specimen 0.001–0.5 ml to the composition for assay of chiroinositol, reacting at 37° C., and measuring an amount of generated A2 or consumed B1 based on changes of absorption during several minutes to several tens minutes between 2 points after constant time from starting the reaction, for example 1 minutes between after 3 minutes and 4 minutes, or 5 minutes between after 3 minutes and 8 minutes. In this case, amount of chiroinositol in the specimens can be assayed by comparing with changes of absorption using known amount of chiroinositol.

The assay method of the present invention is constituted to introduce chiroinositol per se in the specimens into enzyme cycling reaction, and is not affected by coexisting substances in the specimens, consequently blank asssay of the specimens can be omitted and is made possible to simple rate assay.

Reduced coenzyme assay by measuring absorption change used in the present invention can be performed by other known method.

Examples of specimens containing chiroinositol are blood, urine, cerebrospinal fluid, lymph, tissue extracts and food extracts, but can not be limited if it contains chiroinositol.

MODE FOR CARRYING OUT THE INVENTION

Following examples and referential examples illustrate the present invention in details, but are not construed as limiting the present invention.

REFERENTIAL EXAMPLE 1

Culture of Bacillus sp. No. 3 (National Institute of Biosceience and Human-Technology, Agency of Industrial Science and Technology, Ministry of International Trade and Industry, Deposition No. FERM BP-5881).

Liquid culture medium 100 ml containing yeast extract (Kyokuto Seiyaku Co., Japan) 2%, peptone (Kyokuto Seiyaku Co., Japan) 2%, potassium dihydrogen phosphate (Wako Pure Chemicals Inc., Japan) 0.2%, calcium chloride (Wako Pure Chemicals Inc., Japan) 0.02%, magnesium sulfate (Wako Pure Chemicals Inc., Japan) 0.05% and myo-inositol (Wako Pure Chemicals Inc., Japan) 2%, pH 7.3, was poured into 500 ml Erlenmeyer's flask, sterized at 120° C. for 20 minutes. A loopful of Bacillus sp. No. 3 (FERM BP-5881) was inoculated thereto and cultured at 50° C. for 30 hours with shaking at 120 r.p.m. to obtain seed culture 85 ml (enzyme activity 1.9 U/ml).

The liquid culture medium 20 liters, to which anti-form agent Disform 442 (Nihon Yushi Co., Japan) 0.1% was added, containing the same composition of the above, was prepared in 30 L jar fermentor and sterilized by heating. The above seed culture 85 ml was inoculated to the said medium and cultured at 50° C., aeration 20 L/min., inner pressure 0.4 kg/cm$^2$, agitation 150 r.p.m. for 24 hours to obtain cultures mass 18.0 L (enzyme activity 2.9 U/ml).

REFERENTIAL EXAMPLE 2

Cultured cells were collected by centrifugation of the cultured mass obtained in Referential example 1, and 20 mM phosphate buffer (pH 7.5) 5 L containing 0.1% lysozyme (Eisai Co., Japan) was added, then the mixture was incubated at 37° C. for 1 hour. Precipitates was removed by centrifugation to obtain supernatant solution 4.5 L (10 U/ml). Acetone 1.8 L was added to the supernatant solution and stirred to collect the precipitate by centrifugation. The thus obtained precipitated was dissolved in 20 mM Phosphate buffer to obtain crude enzyme, 1 L (39 U/ml). Solid ammonium sulfate 200 g was dissolved in the said solution, the thus formed precipitate was removed by centrifugation, and again solid ammonium sulfate 250 g was dissolved in the thus obtained supernatant solution. The precipitate obtained by centrifugation of the ammonium sulfate treated solution was dissolved in 20 mM phosphate buffer (pH 7.5) to obtain enzyme solution 500 ml (58.1 U/ml). The enzyme solution was concentrated by using UF module (Asahi Kasei Kogyo K.K., Japan, ACF-1010), desalted by using Sephadex G-25 (Pharmacia Inc., Sweden) buffered with 20 mM phosphate buffer (pH 7.5). The solution was charged on a column of DEAE-Sepharose CL-6B (Pharmacia Inc., Sweden) 250 ml buffered with the same buffer, and developed by KCl gradient elution of 0→0.3 M, to collect active peaks and obtain enzyme solution 400 ml (49.3 U/ml). The enzyme solution was dialyzed against 10 mM phosphate buffer (pH 7.0) 20 L for overnight. To the enzyme solution was dissolved bovine serum albumin (Sigma Inc., U.S.A.) 0.2 g, and lyophilized to obtain lyophilized product 1.2 g (17.0 U/mg).

REFERENTIAL EXAMPLE 3

Culture of *Agrobacterium rhizogenes* (National Institute of Bioscience and Human-Technology, Agency of Industrial Science and Technology, Ministry of International Trade and Industry, Deposition No. FERM BP-6270) and purification of the product Liquid culture medium 100 ml containing yeast extract (Kyokuto Seiyaku Co., Japan) 2%, peptone (Kyokuto Seiyaku Co., Japan) 2%, potassium dihydrogen phosphate (Wako Pure Chemicals Inc., Japan) 0.2%, glucose (Kokusan Kagaku Co., Japan) 0.1% and glycerin (Wako Pure Chemicals Inc., Japan) 2%, pH 7.0was poured into 500 ml Erlenmeyer's flask, sterilized at 120° C. for 20 minutes. A loopful of *Agrobacterium rhizogenes* (FERM BP-270) was inoculated thereto and cultured at 28° C. for 30 hours with shaking at 120 r.p.m. to obtain seed culture.

The liquid culture medium 20 liters, to which anti-form agent Disform BC-51Y (Nihon Yushi Co., Japan) 0.1% was added, containing the same composition of the above, from which glucose and glycerin were deleted, was prepared in 30 L jar fermentor and sterilized by heating. The above seed culture 100 ml was inoculated to the said medium and cultured at 30° C., aeration 20 L/min., inner pressure 0.4 kg/cm2, agitation 150 r.p.m. for 24 hours to obtain cultured mass 20 L (enzyme activity 60 mU/ml). Cultured cells were collected by centrifugation of the cultured mass, to which 20 mM phosphate buffer (pH 7.5) 2 L was added, and sonicated for 30 minutes in the ice bath. Precipitates was removed by centrifugation t,) obtain supernatant solution 1.5 L (690 mU/ml).

The enzyme solution was charged on a column of Q-Sepharose big beads (Pharmacia Inc., Sweden) buffered with the same buffer, and stepwisely developed by the same buffer containing KCl of 0, 0.1, 0.2, 0.3 and 0.4 M, to collect 0.4 M fractions to obtain enzyme solution 10 L (4 mU/ml). The thus obtained enzyme solution was concentrated by using UF module (Asahi Kasei Kogyo K.K., Japan, ACP-1010) and dialyzed against 10 mM phosphate buffer (pH 7.5) 10 L for overnight to obtain crude purified enzyme solution 200 ml (270 mU/ml).

REFERENTIAL EXAMPLE 4

Culture of *Streptomyces roseogriseus* (National Institute of Bioscience and Human-Technology, Agenct of Industrial Science and Technology, Ministry of International Trade and Industry, Deposition No. FERM BP-6269) and purification of the product Liquid culture medium 100 ml containing beer yeast extract "Ebios" (Asahi Beer Foods Co., Japan) 2%, magnesium sulfate (Wako Pure Chemicals Inc., Japan) 0.03%, potassium dihydrogen phosphate (Wako Pure Chemicals Inc., Japan) 0.5%, glucose (Kokusan Kagaku Co., Japan) 0.1%, maltose (Nakarai Tesk Co., Japan) 1% and glycerin (Wako Pure Chemicals Inc., Japan) 0.5%, pH 6.5 was poured into 500 ml Erlenmeyer's flask, sterilized at 120° C. for 20 minute's. A loopful of *Streptomyces roseogriseus* (FERM BP-6269) was inoculated thereto and cultured at 28° C. for 120 hours with shaking to obtain seed culture.

The liquid culture medium 20 liters, to which anti-form agent Disform BC-51Y (Nihon Yushi Co., Japan) 0.1% was added, containing the same composition of the above was prepared in 30 L jar fermentor and sterilized by heating. The above seed culture 100 ml was inoculated to the said medium and cultured at 30° C., aeration 20 L/min., inner pressure 0.4 kg/cm$^2$, agitation 150 r.p.m. for 24 hours to obtain cultured mass 20 L (enzyme activity 60 mU/ml). Cultured cells were collected by centrifugation of the cultured mass, to which 20 mM phosphate buffer (pH 7.5) 5 L was added, and sonicated for 30 minutes in the ice bath. Precipitates was removed by centrifugation (7500 r.p.m. for 20 minutes) to obtain supernatant solution 3.0 L (690 mU/ml).

The enzyme solution was charged on a column of Q-Sepharose big beads (Pharmacia Inc., Sweden) 2l buffered with the same buffer, and stepwisely developed by the same buffer containing KCl of 0, 0.1, 0.2, 0.3 and 0.4 M, to collect 0.2 M fractions to obtain enzyme solution 10 L (195 mU/ml). The thus obtained enzyme solution was concentrated by using UF module (Asahi Kasei Kogyo K.K., Japan, ACP-1010) and dialyzed against 10 mM phosphate buffer pH 7.5) 10 L for overnight to obtain crude purified enzyme solution 200 ml (690 mU/ml). The obtained enzyme solution, to which NaCl (Nakarai Tesk Co., Japan) was added for 4 M concentration, was charged on a column of phenyl-Sepharose FF (Pharmacia Inc., Sweden) 150 ml buffered with 10 mM phosphate buffer (pH 7.5) containing 4 M NaCl, developed with NaCl gradient solution of 4→0 M, pooled the active peaks to obtain the enzyme solution 360 ml (1.4 U/ml).

The obtained enzyme solution was dialyzed against 10 mM phosphate buffer (pH 7.5) 10 L for overnight, and charged on a column of DEAE-Sepharose FF (Pharmacia Inc., Sweden) 150 ml buffered with the same buffer solution, then developed with the same buffer containing 0→0.5 M of KCl, pooled the active peaks to obtain enzyme solution 100 ml (2.4 mU/ml). The obtained enzyme solution was dialyzed against 5 mM Tris-acetate buffer (pH 6.5) 10 L for for overnight, and charged on a column of hydroxylapatite (Asahi Pentax Co., Japan) 50 ml buffered with the same buffer solution, then developed with the same buffer containing 0→30 mM of phosphate, pooled the active peaks to obtain enzyme solution 135 ml. The thus obtained enzyme solution was dialyzed against distilled 10 L and concentrated with membrane by which molecular weight was cut at 30,000 to 25 ml (2.5 U/ml). The concentrate was freezing stored as a purified enzyme solution.

EXAMPLE 1

<Reaction system>

| | |
|---|---|
| 0.2 M | glycine-NaOH buffer pH 9.8 |
| 100 U/ml | dehydrogenase which caalyses chiroinositol (*Bacillus sp.* No.3 origin) |
| 0.03 mM | NADH (Oriental Yeast Corp., Japan) |
| 2.0 mM | thio-NAD (Oriental Yeast Corp., Japan) |

<Operation>

Figure 4:
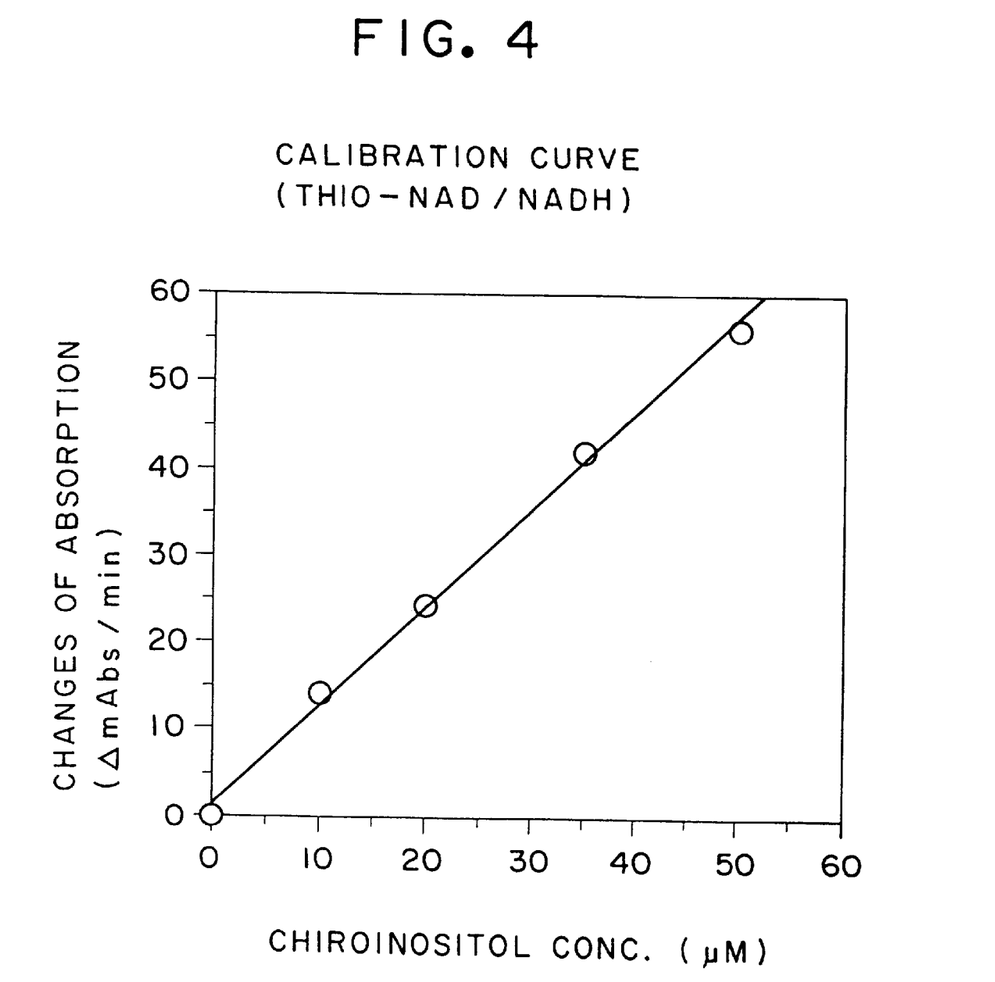
FIG. 4 shows calibration curve of chiroinositol of the present invention.

The above reagent 1 ml was set in a cuvette, added 0, 10, 35 and 50 μM of D-chiroinositol (Wako Pure Chemicals Inc., Japan), respectively, 20 a l and initiated reaction at 37° C. Absorption at 405 nm between after 1 minute and 3 minutes and its difference was observed to obtain changes of absorption per minute. Results are shown in FIG. 4. As shown in FIG. 4, changes of absorption for amount of chiroinositol are indicated good linearity.

EXAMPLE 2

<Reaction system>

| | |
|---|---|
| 0.2 M | glycine NaOH buffer pH 9.8 |
| 100 U/ml | dehydrogenase which catalyses chiroinositol (*Bacillus sp.* No.3 origin) |
| 0.03 mM | NADH (Oriental Yeast Corp., Japan) |
| 2.0 mM | thio-NADP (Oriental Yeast Corp., Japan) |

<Operation>

Figure 5:
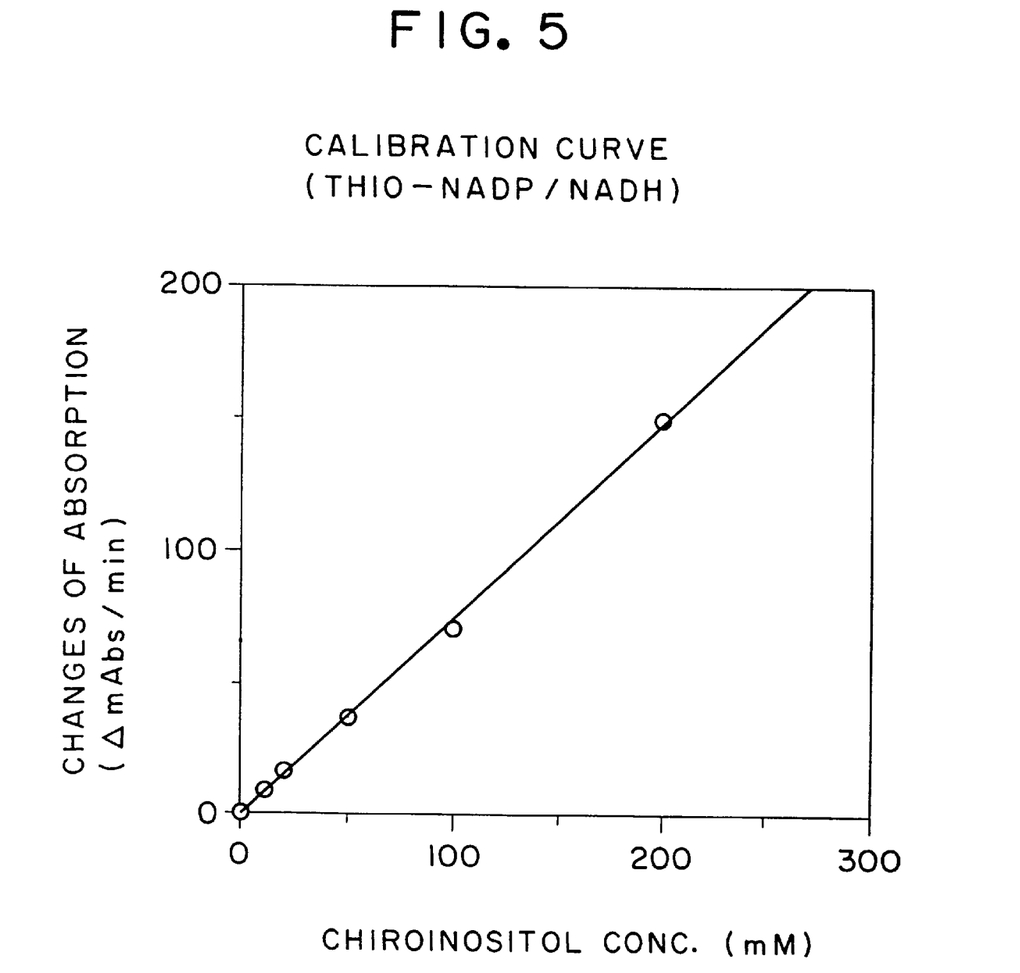
FIG. 5 shows calibration curve of chiroinositol of the present invention.

The above reagent 1 ml was set in a cuvette, added 0, 10, 20, 50, 100 and 200 mM of D-chiroinositol 20 μl and initiated reaction at 37° C. Absorption al 405 nm between after 1 minute and 3 minutes and its difference was observed to obtain changes of absorption per minute. Results are shown in FIG. 5. As shown in FIG. 5, changes of absorption for amount of chiroinositol are indicated good linearity in the cycling reaction with coenzymes thio-NADP/NADH.

EXAMPLE 3

<Reaction system>

| | |
|---|---|
| 0.2 M | glycine-NaOH buffer pH 9.8 |
| 100 U/ml | dehydrogenase which catalyses chiroinositol (*Bacillus sp.* No.3 origin) |
| 0.03 mM | deamino-NADH (Sigma Inc., U.S.A) |
| 2.0 mM | thio-NAD (Oriental Yeast Corp., Japan) |

<Operation>

Figure 6:
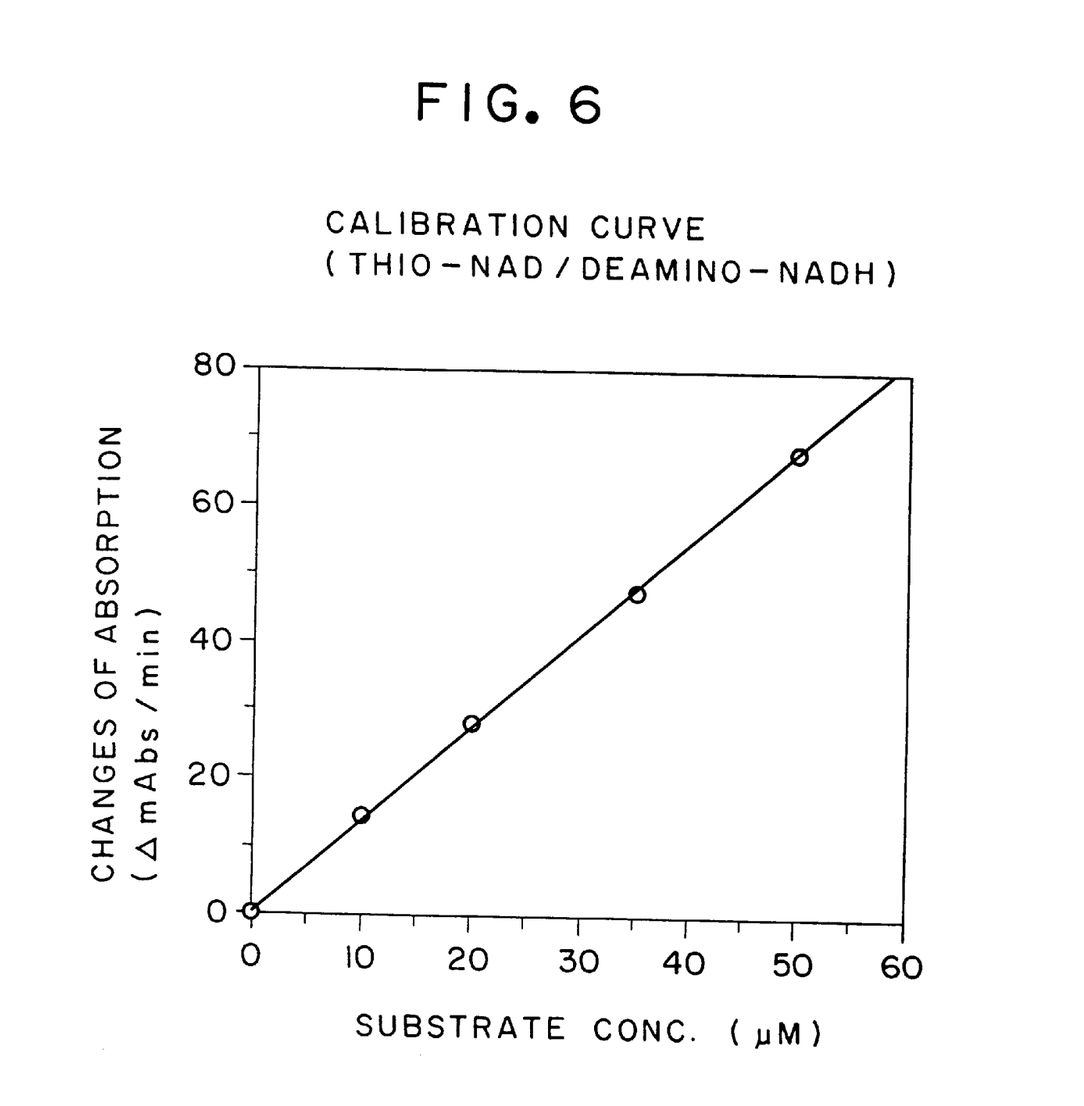
FIG. 6 shows calibration curve of chiroinositol of the present invention.

The above reagent 1 ml was set in a cuvette, added 0, 10, 20, 35 and 50 μM of D-chiroinositol 20 μl and initiated reaction at 37° C. Absorption at 405 nm between after 1 minute and 3 minutes and its difference was observed to obtain changes of absorption per minute. Results are shown in FIG. 6. As shown in FIG. 6, changes of absorption for amount of chiroinositol are indicated good linearity in the cycling reaction with coenzymes thio-NAD/deamino-NADH.

EXAMPLE 4

<Reaction system>

| | |
|---|---|
| 0.2 M | glycine-NaOH buffer pH 9.8 |
| 100 U/ml | dehydrogenase which catalyses chiroinositol (*Bacillus sp.* No.3 origin) |
| 0.03 mM | NADH (Oriental Yeast Corp., Japan) |
| 2.0 mM | thio-NAD (Oriental Yeast Corp., Japan) |

<Operation>

The above reagent, 1 ml was set in a cuvette and preincubated at 37° C. Each 33 μl of urine or serum specimen and initiated reaction at 37° C. Absorption at 405 nm between after 1 minute and 3 minutes and its difference was observed to obtain changes of absorption per minute. The same operations were performed for the standard solution of 20 μM D-chiroinositol and a reagent blank, to which distilled water was added in place of specimens. Concentration of chiroinositol in each sample was calculated from the absorption difference of the standard solution to obtain the results shown in Table 4.

TABLE 4

|  | difference in absorption (ΔmAbs/min) | replaced conc. for chiroinositol (μM) |
|---|---|---|
| blank for reagent | 0.3 | 0.0 |
| control serum 1 | 0.9 | 0.3 |
| control serum 2 | 1.1 | 0.5 |
| urine 1 | 46.7 | 34.8 |
| urine 2 | 14.4 | 10.8 |
| urine 3 | 131.4 | 98.0 |

In Table 4 : control serum 1 ; BML Corp. CL, Japan, and control serum 2 ; Nissui Pharm. Co., Suitorol, Japan.

EXAMPLE 5

| <Reaction system> | |
|---|---|
| 280 mM | glycine-NaOH buffer pH 9.0 |
| 140 U/ml | dehydrogenase which catalyses chiroinositol (*Bacillus sp.* No.3 origin) |
| 0.042 mM | NADH (Oriental Yeast Corp., Japan) |
| 2.8 mM | thio-NAD (Oriental Yeast Corp., Japan) |
| <Operation> | |

Aqueous solution of 1.5 M sodium carbonate (Wako Pure Chemicals Inc., Japan) was added to the above reagent to prepare containing 300 mM sodium carbonate (pH 9.0). A reagent without containing sodium carbonate was prepared as a control. The pH of these reagents, each 2 ml, was measured immediately after preparation and after allowing to stand in the open air at 4° C. for 110 hours.

A pH of the reagent without addition of sodium carbonate was pH 9.01 immediately after preparation, whereas it was decreased to pH 8.51 (24° C.) after storage for 110 hours in the dark. The pH 9.02 thereof with addition of sodium carbonate immediately after preparation was not changed to pH 9.06 (24° C.) after storage for 110 hours in the dark to show keeping stable pH value.

The activity was measured by using the above reagent according to the method described in example 4, in which 35 μM D-chiroinositol was used as a substrate with enzymatic cycling.

In the sodium carbonate addition group, absorption change of 38 mAb/min. was obtained, and in the control group, absorption change of 28 mAb/min. was obtained. This result indicated that the reagent containing hydrogen carbonate ion could prevent pH change as well as showing improved ability for assay of the reagent.

Effect of the invention

As shown in the above, the present invention provide rate assay of the reduced coenzyme and the blank assay for the specimen can be ommitted. Consequently, simple assay can be performed, and sensitivity of assay can be increased by combining cycling reaction thereto. As a result, trace amount of chiroinositol in vivo can be assayed with simple and accurate manners.

We claim:

1. An assay method of chiroinositol which comprises reacting specimen with 1) a dehydrogenase, which catalyzes at least reversible reaction with a substrate of chiroinositol in the presence of a coenzyme selected from nicotinamide adenine dinucleotides (phosphate), hereinafter designates as NAD(P)s and a coenzyme selected from thio-nicotinamide adenine dinucleotides (phosphate), hereinafter designates as thio-NAD(P)s, 2) A1 and

3) B1 to form cycling reaction of the formula wherein a product is a compound, from which 2 or 4 hydrogen atoms are deleted from chiroinositol, A1 is NAD(P)s or thio-NAD(P)s, A2 is a reduced form of A1, B1 is a reduced form of NAD(P)s in case of A1 being thio-NAD(P)s or a reduced form of thio-NAD(P)s in case of A1 being NAD(P)s and B2 is an oxidized form of B1, and determining an amount of converted A2 or B1 by the said reaction.

2. The assay method of chiroinositol according to claim 1 wherein dehydrogenase for chiroinositol is originated from Bacillus sp. No. 3 (FERM BP-5881).

3. The assay method of chiroinositol according to claim 1 wherein the, reaction is performed with containing soluble hydrogen carbonate salt which can release hydrogen carbonate ions.

4. A composition for assay of chiroinositol comprising the following components:

1) a dehydrogenase, which catalyses at least reversible reaction with a substrate of chiroinositol in the presence of a coenzyme selected from nicotinamide adenine dinucleotides (phosphate), hereinafter designates as NAD(P)s and a coenzyme selected from thio-nicotinamide adenine dinucleotides (phosphate), hereinafter designates as thio-NAD(P)s, 2) at least a coenzyme selected from NAD(P)s and thio-NAD(P)s, and 3) in the above 2), at least a coenzyme selected from reduced thio-NAD(P)s in case of at least a coenzyme selected from NAD(P)s, or in the above 2), at least a coenzyme selected from reduced NAD(P)s in case of at least a coenzyme selected from thio-NAD(P)s.

5. The composition for assay of chiroinositol according to claim 4 further comprising soluble hydrogen carbonate salt which can release hydrogen carbonate ions.

* * * * *